United States Patent [19]

Kino et al.

[11] Patent Number: 4,503,708
[45] Date of Patent: Mar. 12, 1985

[54] REFLECTION ACOUSTIC MICROSCOPE FOR PRECISION DIFFERENTIAL PHASE IMAGING

[75] Inventors: Gordon S. Kino, Stanford; Butrus T. Khuri-Yakub; Simon D. Bennett, both of Palo Alto; Kenneth K. Liang, Menlo Park, all of Calif.

[73] Assignee: Board of Trustees of the Leland Stanford Junior University, Stanford, Calif.

[21] Appl. No.: 464,394

[22] Filed: Feb. 7, 1983

[51] Int. Cl.³ .............................................. G01N 29/00
[52] U.S. Cl. ......................................... 73/628; 73/606
[58] Field of Search ................. 73/628, 629, 605, 606, 73/607

[56] References Cited

FOREIGN PATENT DOCUMENTS 2821574 5/1977 Fed. Rep. of Germany ........ 73/607

OTHER PUBLICATIONS

"Oblique Incidence Reflection Acoustic Imaging", C. E. Yeack and M. Chodorow, *Journal Appl. Phys.*, pp. 4637–4638, Sep. 1980.

*Primary Examiner*—Stephen A. Kreitman
*Attorney, Agent, or Firm*—Flehr, Hohbach, Test, Albritton & Herbert

[57] ABSTRACT

An acoustic microscope comprising a transducer for transmitting acoustic signals towards the surface to be studied, and means for receiving at least one reflected signal from the surface; in many embodiments of the invention, signals are received from two separate points. The signals received are passed to a synchronous phase detection system for analysis. The signals may be received at the same phase detector input and separated according to their expected time of receipt relative to their time of transmission, or they may be received at separated points on the transducer related to their separated points of transmission. The separated return signals are compared on the basis of phase (and in certain embodiments, magnitude) differential either to each other or to an internally generated reference signal to analyze the surface characteristics of the material.

24 Claims, 9 Drawing Figures

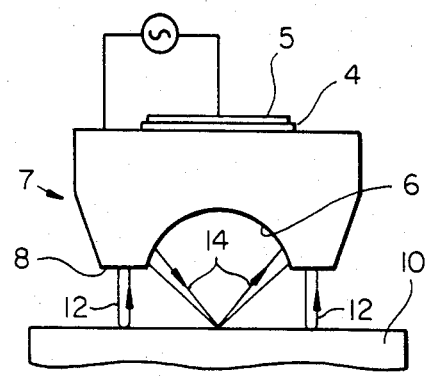
FIG_1A
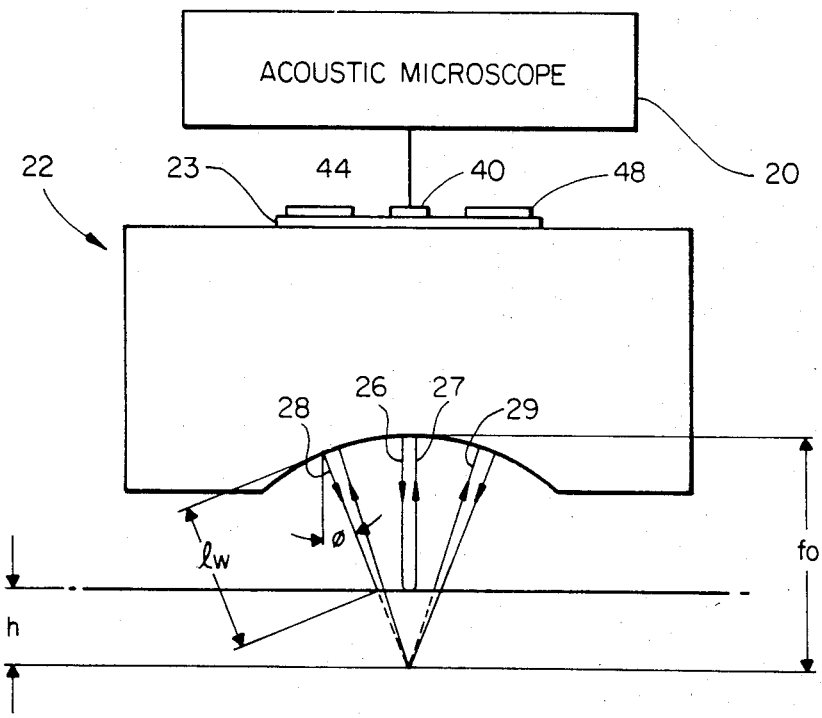
FIG_1B

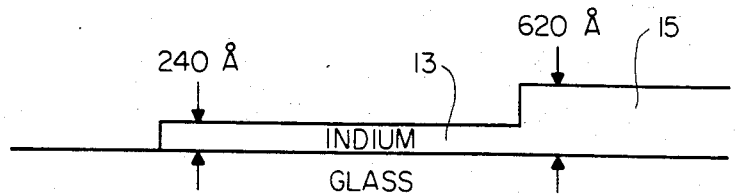
FIG_2A
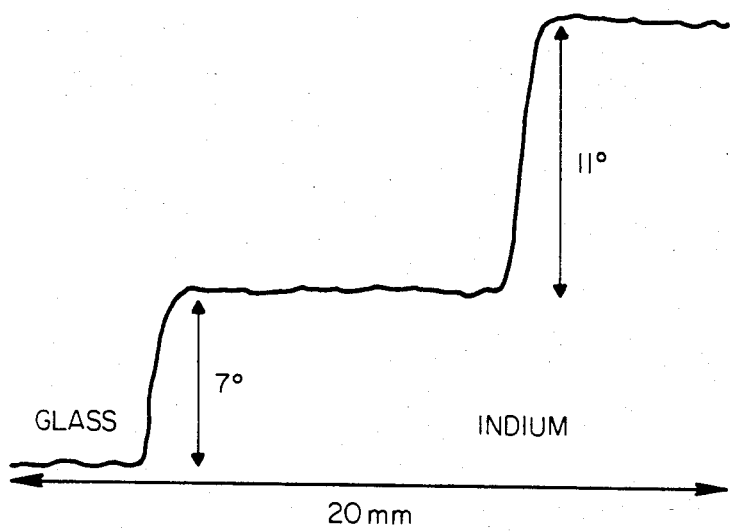
FIG_2B
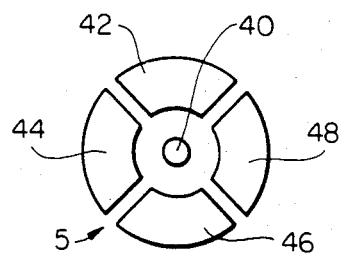
FIG_3

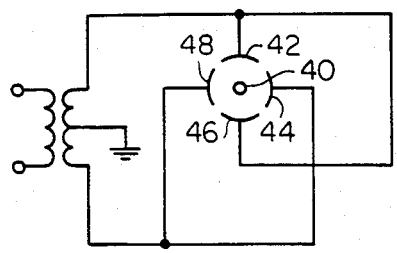
FIG_4A
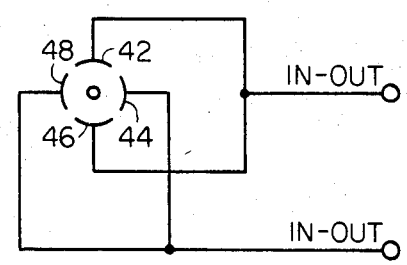
FIG_4B
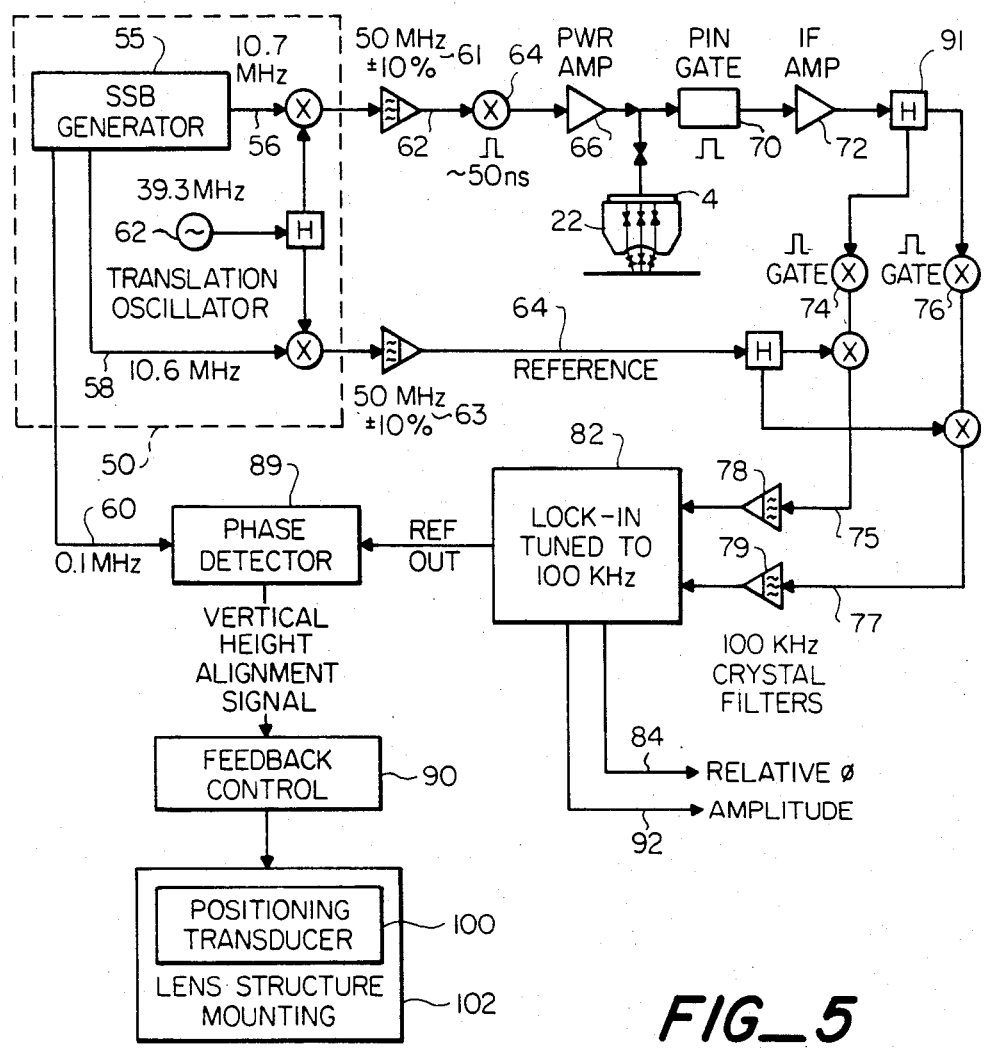
FIG_5

REFLECTION ACOUSTIC MICROSCOPE FOR PRECISION DIFFERENTIAL PHASE IMAGING

GOVERNMENT CONTRACT

The present invention was developed in the course of work funded by the Air Force Office Of Scientific Research under contract F 49620-79-C-0217 awarded by the U.S. Air Force. The government has certain rights in this invention.

BACKGROUND OF THE INVENTION

1. Field of the Invention

The present invention generally relates to microscopic acoustic measurements, especially the measurement of phase differences in reflected acoustic waves to define distances, velocities, or surface characteristics with very high accuracy.

2. Description of the Prior Art

In 1975 R. A. Lemmons and C. F. Quate invented the scanning acoustic microscope. In this device a high frequency plane wave is focused by an acoustic lens to scan an object located at the focal point of the lens. The acoustic waves either are transmitted through or reflected by the object. In either case, the acoustic waves are thereafter recollimated by a second acoustic lens and are detected with a piezoelectric detector. The detected signals are applied to an oscilloscope to provide a visual display of the object. This device is further described in the Lemmons and Quate patent entitled Acoustic Microscope, U.S. Pat. No. 4,028,933 issued June 14, 1977. In addition, an apparatus of this type is described in the article, "Acoustic Microscopy: Biomedical Applications", by Lemmons and Quate in *Science*, 188, pp. 905-911, May 30, 1975, and in the article, "Acoustic Microscopy at Optical Wavelengths", by V. Jibsom and C. F. Quate, *Applied Physics Letters*, 32 (12) pp. 789-791, June 15, 1978. A more complete collection of articles discussing acoustic microscopy can be found in the preamble of U.S. Pat. No. 4,267,732.

A variety of efforts have been made to utilize such apparatus to analyze the surface structure of materials. For example, in a Quate patent U.S. Pat. No. 4,267,732, the apparatus there includes devices for exciting an object of interest so that acoustic waves are propagated from the object. A wave detector and the object are moved with respect to each other in a raster scan pattern so that a visual image can be obtained. In addition, the frequency of the exciting radiation is varied so that the absorption spectra and the Raman frequency mode of the object can be determined.

In a further example, wherein the surface structure of semiconductors and integrated circuits are analyzed for defects, the integrated circuit may be energized by a pulsating electric current with the resistive heating of the circuit being observed. In another embodiment, light propagated through the back of the semiconductor wafer and the resulting acoustic waves propagated through the front surface are imaged and measured.

It is the general objective of the present invention to improve the accuracy of surface measurement techniques in the field of acoustic microscopy by providing a method of, and apparatus for acoustic imaging which uses signals transmitted from a transducer to measure the surface characteristics of a material by establishing the phase shift of the return signals from the material relative to some reference signal.

It is a further object of the invention to use the reflected signal return to accurately measure and maintain constant the distance between the transducer and the object surface to be studied. In a preferred embodiment of this invention, the material surface to be studied is located at the focal plane of the lens.

It is yet another object of the invention to provide pulse transmitting, and receiving means and analyzing means for developing and analyzing the Rayleigh wave characteristics of the material, especially by measuring phase shift in the signal returns from a material substrate located within the focal plane of the transducer.

It is another object of the invention to provide a new structural form of transducer for transmission of at least two separate signals to be used to determine the distance from the transducer to the object surface and/or the wave perturbation along the object's surface. These and other objects are achieved by an acoustic microscope comprising a transducer for transmitting acoustic signals towards the surface to be studied, and means for receiving at least one reflected signal from the surface; in many embodiments of the invention, signals are received from two separate points. The signals received are passed to a synchronous phase detection system for analysis. The signals may be received at the same phase detector input and separated according to their expected time of receipt relative to their time of transmission, or they may be received at separated points on the transducer related to their separated points of transmission. The separated return signals are compared on the basis of their phase differential either to each other or to an internally generated reference signal to analyze the surface characteristics of the material.

For example, minute changes in surface profile or depth profile on the surface of the material can be identified by analysis of the phase shift of the reflected return wave relative to the transmitted wave. In another mode of operation, the velocity of Rayleigh waves traveling along the surface is measured by measuring phase differences of acoustic waves. The relative velocity or phase differential between the originated surface wave and a reference signal is a direct indication of the constituency of the surface through which the waves pass. The waves will travel at different speeds if traveling through a film that adheres well to a surface or one that is somewhat separated from the surface, thereby giving important indicators on data that is highly desirable in the manufacture of devices wherein thin layers are laid down one atop the other, as in the manufacture of integrated circuits.

As a further improvement over known systems for acoustic measurement, a phase lock loop control mechanism is incorporated in the measurement system to establish and maintain a constant distance between the lens and the substrate. This improvement is necessary because the measured phase of the reflected signals is affected by the distance between the acoustic lens and the substrate, which may be changed by ambient temperature drift and/or minor topographical changes in the sample surface. With the addition of the phase lock loop distance control system described in detail below, the phase measured is truly due to the surface material property with no artifacts introduced by topographical variation. Alternatively, this phase lock loop distance measuring system may, when combined with surface scanning means, be used as an unusually accurate way of measuring topographical variations in the surface.

The measurement technique described herein is much more direct and orders of magnitude more accurate than existing techniques based on obtaining the so-called V(z) curve as the material signature.

As a further refinement in the system, a new transducer is described herein incorporating separate electrodes, i.e., a center electrode for the on-axis transmission and reception and an outer concentric ring electrode for the generation and detection of signals which comprise the Rayleigh path signals. The ring electrode may alternatively be divided into segments, with opposite ones wired together in order to propagate waves in a number of different directions. With this modification the system comprises a scanning acoustic microscope ideally suited for analyzing surface properties in two dimensions. In a further embodiment, the ring electrode may be used solely to transmit and receive the distance-measuring reference signals.

CROSS-REFERENCE TO RELATED APPLICATIONS

Acoustic microscopes, their essential elements and fundamental mode of operation are shown, for example, in U.S. Pat. No. 4,012,950 and U.S. Pat. No. 4,011,748 which are incorporated herein by reference.

BRIEF DESCRIPTION OF THE DRAWINGS

FIG. 1 is a model of an acoustic transducer having its focal point at the surface of the substrate; FIG. 1B is a model of a basic acoustic microscope having its transducer structure focused below the substrate, and including A. FIG. 1C is a ray model of the microscope transducer showing the significant contributing rays to the transducer output.

FIGS. 2A and 2B illustrate a typical substrate surface having a film thereon, and the measured phase shift in the signal returns to the transducer of FIG. 1B.

FIG. 3 is a topographical view of a modified set of electrodes for the transducer of FIG. 1B.

FIGS. 4A and 4B illustrate alternative circuit configurations for quantitative measurements with the acoustic microscope.

FIG. 5 illustrates a phase detection scheme for precise phase measurement with the acoustic microscope of this invention.

DESCRIPTION OF A PREFERRED EMBODIMENT

The subject invention is directed to means and a method for determining by measuring at localized places on a sample or substrate 10 a change in phase between a reference signal and a reflected signal. As a result, a constant indication of the distance between the transducer and the surface being imaged can be calculated, or alternatively, changes in surface characteristics of the sample can be measured.

A basic application of this phase differentiation from the technique is shown in FIG. 1A. FIG. 1A shows a transducer which is the signal transmitting and receiving portion of an acoustic microscope (not shown) having a top electrode 5 thereon for exciting the transducer 4 and receiving the reflected signals. The lens structure comprises at least a concave portion 6, which may be cylindrical or spherical, and an outer planar portion 8 which may be used for sending signals to a substrate 10 which is to be measured. (The width of the planar portion is exaggerated here). The portions of the lens structure 7 being used to send and receive signals depends on the alignment, form and excitation of the electrode 5 to excite transducer 4. In a basic application of the acoustic phase imaging technique, the substrate 10 is placed at the focal plane of the transducer 4. The reference signal is basically the signal 12 which in this embodiment is shown transmitted from each outer portion of the lens structure 7. Alternatively the reference signal 12 may be transmitted from the central portion of the substrate concave portion 6 by selective excitation thereof from electrode 5. A separate signal ray 14 is transmitted from the concave portion of the lens to the substrate at a defined angle $\phi$. By measuring the phase difference of the returned focused ray 14 and the reference ray 12 utilizing a phase comparator circuit defined in detail below, a measurement may be developed to establish variations in the distance of the transducer and lens structure 7 from the substrate 10. Therefore, based on the known beginning phase difference and any variation in phase difference between the two rays 12, 14 that pass through the portion of the lens structure normal to the substrate ring 8 and the portion of the lens 6 which transmit rays at an angle to the substrate, the variation in the height of a series of points on the substrate 10 can be measured to accuracy corresponding to a very small fraction of a wavelength. Thus by scanning the system across the surface of a substrate 10, very small variations in surface height of the substrate 10 can be measured. In a preferred embodiment, this phase shift information is fed back to a second piezoelectric transducer 100 located in the mounting which supports lens structure 7. The vertical height alignment signal 90 developed by the network of FIG. 6 in addition to being recorded, is fed back to this transducer 100. The position of lens structure 7 relative to the surface of substrate 10 will be adjusted in response to this signal to positioning transducer 100 so that the surface of the substrate 10 at the point under examination always lies on the focal plane of the rays from line 6.

In a second embodiment of this invention, a technique is explored for imaging variation in the surface characteristics of a sample by measuring the local perturbation of the Rayleigh wave velocity, utilizing an acoustic microscope 20 and transducer-lens structure 22. In this second embodiment, the transducer 23 is excited by electrodes indicated generally at 24 and to be described with greater particularity below. A very short tone burst provided by the acoustic microscope 20 produces on-axis and off-axis waves 26 and 28, respectively, as shown in FIG. 1B. The on-axis wave 26 is directly reflected back to the lens-structure 22 and detected using the transducer 23 and electrode 24. The off-axis wave 28 is propagated along the surface of the substrate 10 and is reflected back to the lens structure 22 for detection by the transducer 23 and electrode 24. The two return signals 27 and 29 are temporally separated tone bursts. The relative phase between the two return signals 27 and 29 is accurately measured using a phase detection scheme shown in FIG. 5 and to be described in detail below. The phase difference between the normally reflected ray 27 and the off-axis reflected ray 29 can be used to generate information about the velocity of the Rayleigh wave through the substrate which in turn can be analyzed to provide significant understanding of the properties of the medium through which the Rayleigh wave has traveled.

This phenomenon of Rayleigh wave travel through a medium using a wave generated by an acoustic microscope has been published in a report entitled, "Microwaves, Acoustics And Scanning Microscopy", by C. F. Quate which appears in the proceedings of the Rank Prize International Symposium On Scanned Image Microscopy and which is incorporated herein by reference as an explanation of the underlying acoustic microscope phenomena related to Rayleigh wave travel. While this paper provides a theoretical discussion, it contains no enabling disclosure of the phenomena discussed. It is the object and intent and contribution of the subject invention to provide means for accurately analyzing these phase differences and utilizing the phase differences to develop significant usable information about the substrates through which such Rayleigh waves are propagated.

An example of the use of this embodiment of FIG. 1B to analyze the surface characteristics of a sample is described in greater detail below.

EXAMPLE 1

The test object was a multiple thickness indium film, shown in FIG. 2A. The thicknesses of the film layer portions 13 and 15 were 240 angstroms and 620 angstroms, respectively. The indium film overlay 13 caused a perturbation of the Rayleigh wave velocity on the glass substrate to be measured. The line scan exhibited a phase change in the reference signal 12 relative to the reference signal 14 (FIG. 1A) of 7° for the 240 angstrom step change from glass to indium and another 11° for the 380 angstrom step change in indium thickness. It can be calculated to a first order that the velocity perturbation on glass due to the indium overlay is about 0.18% for the 240 angstrom layer and 0.46% for the 620 angstrom layer. The spatial resolution of the system is determined from the transition of the steps in the line scan to be about 1 mm. which gives a rough estimate of the length of the Rayleigh wave pattern along the water solid interface.

Based on this estimate and the theoretically derived velocity perturbation, one would expect changes of 9.5° and 15° for the 240 angstrom and 380 angstrom step transitions, respectively. The experimentally measured results are somewhat lower than the calculated phase changes but the two sets of results are consistent in that the percentage differences between them is the same for the two step changes in thickness. It is believed that the discrepancy is due to the uncertainty in the estimation of the Rayleigh wave path length and the properties of the indium film. A further modification in the accuracy of the system may also be achieved by modification of the time separation between the on-axis reflection signal and the Rayleigh wave path signal pulses.

A modified electrode 5 has been developed for generation of the rays from transducer 2 in FIG. 2a, for measurement of these surface characteristics using the phenomena described. An exemplary embodiment of this electrode is shown in FIG. 3 and comprises a center section 40 and ring sections 42, 44, 46 and 48. These sections can also be seen having been given the same numbers in the sectional view which comprises FIG. 1B where the center electrode is labeled as 40 and two of the opposing outer electrodes are labeled 44 and 48. This electrode modification was adopted in response to the fact that in order to achieve better spatial definition in the measurement of the phase differential between the normal and the Rayleigh wave reflections, the sample surface should be located closer to the focal plane of the lens, which also results in a corresponding reduction of the time separation (and phase differential) between the on-axis reflection and the Rayleigh path signal pulses 27 and 29. As the surface of the material being examined is moved closer to the focal plane, the pulses tend to overlap in time. Since in the phase detection system to be described in detail below, in at least one embodiment which utilizes a single electrode to excite the transducer, they are picked up on the same electrical channel, it becomes extremely difficult to separate them physically to make precise phase measurements.

In the modified electrode shown in FIG. 4, the transducer is excited with electrodes 40–48 to process separately the two signals of interest. A small center electrode 40 is used just for the on-axis reflection signal and the outer electrode which overlies the portion of the transducer used to transmit and detect off-axis rays is used exclusively for the Rayleigh path signal. Since the signals are now physically separated to begin with, the time overlap problem is diminished. Consequently, the sample 10 of interest can be moved closer to the focal plane of the lens to achieve better spatial resolution by shortening the Rayleigh wave path on the surface of the substrate. The penalty, of course, is a loss in phase resolution because of the shorter Rayleigh path and therefore a diminished phase differential between the on-axis reflection and Rayleigh reflection. Nevertheless, in any practical application where a high degree of phase accuracy is not needed, the large reserve of phase sensitivity inherent in the measurement system described herein can be traded for spatial resolution. In a preferred embodiment of the electrode, the ring electrode is segmented into diametrically opposed pairs which are multiplexed as shown in FIGS. 5A and 5B to launch Rayleigh waves in different directions; in this manner phase shift differences in both the x and y directions along the substrate surface can be measured so that two dimensional surface mapping is achieved. Alternatively, or in addition to use of the modified electrode system, the spatial resolution of this system can be improved by using higher frequency transducers than the ones described in the preferred embodiment herein. When used with the same percentage bandwidth, since the impulse response is more compact in time, the sample can be located closer to the focal plane to better the spatial resolution while maintaining adequate time separation between pulses of interest. There is no loss in phase sensitivity because at a high frequency of operation the same number of acoustic wavelengths is compressed into a shorter Rayleigh path.

In considering what configuration of electrodes should be used, it should be noted that most embodiments of the invention utilized rays transmitted normal to the surface from the transducer such as ray 12 in FIG. 1A or ray 26 in FIG. 1B, signal returns from which will establish reference data, and rays such as ray 14 in FIG. 1A or ray 28 in FIG. 1B transmitted at an angle $\phi$ with the substrate to generate Rayleigh wave or other signal return data, the phase shift in the angled signal return relative to the normal signal-return being of significance. The exciting electrodes must overlay the portions of the transducer surface being used to transmit and receive rays. The electrodes may constitute a ring and separate center portion as in FIG. 1B; or a segmented ring as shown in FIG. 3; or the outer electrodes may be linear in shape, lying across the axis of interest along which exploration of substrate 10 is to be carried out. The lens 6 itself may be cylindrical or spherical shaped depending on the axis of interest for exploration.

Returning to the overall system shown diagrammatically in FIG. 1B, when the acoustic lens is placed with its focal point below the surface of the substrate 10, the significant contributions to the phase differential which is to be measured utilizing the electrical output through electrodes 40, 42 and 44 are the on-axis or normal ray 27 and the outer ray 29 which impinges on the water solid interface at the Rayleigh angle and excites a leaky surface wave 29 which reradiates back to the acoustic lens 22 of transducer 23. Since the two contributions are, in the simplest example, picked up on the same electrical channel, i.e., picked up by a transducer as shown in FIG. 5 and indicated at 22 having a single electrical output, they interfere to give rise to periodic maxima and minima as the lens is moved in and out of focus, yielding the so-called V (z) curve which is theoretically developed in the Quate article incorporated above. The surface wave velocity theoretically can be calculated by measuring the interval between the minima on this wave. However, this measurement technique lacks precision because it is difficult to pinpoint exact locations of the minima due to the presence of noise.

In a major departure from the teachings of the Quate article, the subject invention, therefore uses a technique based on the consideration that the propagation time difference between the on-axis reflection signal at 27 and the Rayleigh wave path reflection signal 29 can be substantial if the amount of defocussing is large, i.e., if the ratio of h, that is, the distance below the surface of the subtrate to the focal plane to $f_o$ which is the true focal length is greater than 0.1. When a broadband transducer 22 is excited with a sufficiently short duration pulse generated by the gate 64 which modulates the output of the single side band generator 50 of FIG. 5, the temporally separated signals from the two ray paths 27, 29 can be isolated electrically with the power splitter 91 and the gates 74, 76 (FIG. 5). Since the signal pulses are thus distinct and separable, one can in principle, measure the time difference or correspondingly the phase difference between them. The relative phase so obtained is closely associated with the Rayleigh velocity of a wave on the surface of the Sample 10. Even more importantly, the change in phase, $\Delta\phi$, as the lens is moved over a surface at a constant distance away from it using the means previously described, is directly related to the change in surface wave velocity.

The reflection acoustic microscope shown in FIG. 1B is specifically designed for precision differential phase imaging based on clearly defining the phase differences between the on-axis and off-axis wave reflections. The system of FIG. 5 consists of two basic components, i.e., a mechanically scanned acoustic microscope 20 as known generally in the prior art and a precision synchronous phase detector 51 as now herein described. The acoustic microscope consists in a preferred embodiment of a 50 Megahertz lithium niobate transducer 4 bonded to a fused quartz buffer rod 7. The radius of curvature of the spherical lens 6 ground in the front face of the quartz rod 7 is 3.175 mm. resulting in a focal length ($f_o$) of 4.25 mm. in water. The lens 6 with an aperture of 6 mm. is fully illuminated by the transducer and thus produces a wide enough cone of insonification to accommodate materials with surface wave velocities greater than 2.2 km./s. The specimen 10 under inspection is typically positioned 1-2 mm. above the focal plane to provide sufficient temporal separation between the on-axis longitudinal response 27 and the Rayleigh wave path reflection 29 for the time gating on reception. A typical separation between pulses is about 200 ns.

The synchronous phase detector of this invention consists of a single side band generator 50 which includes a generator 55 for generating three output signals: one of 10.7 Megahertz on output line 56; one of 10.6 Megahertz on an output line 58; and one of 0.1 Megahertz on an output line 60. The signals on lines 56 and 58 are combined with the signal output of a free running translation oscillator 62 to form a 50 Megahertz cw signal on a line 62 and a 49.9 Megahertz synchronous reference on a line 64. The 50 Megahertz signal 61 on line 62 is applied via a gate 64 and a power amplifier 66 to the transducer 20. The gate 64 gates the 50 Megahertz signal to provide a three cycle tone burst which drives the transducer 4. The longitudinal and Rayleigh path return echoes 27 and 29 from sample 1 are separated by a gate 70 and then passed through IF amplifier 72 to separating gates 74 and 76. The outputs of gates 74 and 76 are combined with the 49.9 Megahertz reference 63 on line 64 to create a frequency spectrum centered on 100 kilohertz. The 100 kilohertz signals on lines 75 and 77 are passed through 100 kilohertz crystal filters 78 and 79 to select the 100 kilohertz component which is then fed to a lock-on amplifier 82 tuned to 100 kilohertz for phase comparison. The lock in amplifier 82 (which like the other components in this system is of known design), compares the signal outputs of the two crystal filters 78 and 79 to define the relative phase of the two signals which appears on output 84. The amplifier 82 also detects any change in amplitude between the two signals, which amplitude data can also be used for analysis of the characteristics of the substrate 10. As explained above with reference to FIGS. 1 and 2, the phase distinction is also related to the distance between the lens 22 and the specimen 1 or equivalently, the defocussing distance h.

This distance h is extremely sensitive to temperature variations in the mounting structure and water path. To eliminate the effects of thermal drift, a feedback control mechanism is incorporated in this system to improve its accuracy even further. In this feedback control mechanism 90 compensation is accomplished by comparing the phase of the on-axis longitudinal reflection on one of lines 75 and 77 against the synchronous electronic temperature stable reference signal appearing on line 60 from the original single side band generator 55 which is used to generate the same signal which drives the transducer. The position of the transducer and lens structure 20 is continuously adjusted vertically, thereby adjusting the distance h by a piezoelectric means 100 of known construction incorporated in the housing of transducer 20 to keep a constant phase relationship between acoustic and electronic signals. This feature also provides in a system where the transducer structure is being scanned across a surface of a substrate 10, a means for tracking the surface topography of the sample as discussed with respect to FIG. 1A. Hence, by utilizing the phase detector 89 and feedback control 90, the phase information obtained by the measurement is truly related only to the material property of the surface.

This phase measurement technique is a precise and direct means of mapping velocity perturbation on a surface as compared to the usual procedure of measuring intervals between nulls of the V(z) curve as described in the above referenced Quate article. If one should be interested in the absolute Rayleigh velocity, a careful V(z) measurement could be carried out at some reference position on the sample, and the differential phase measurement would yield the velocity distribution over the surface.

Using this technique we measure the amplitude and phase of the V(z) curve. This makes it possible to use Fourier transform technique to obtain detailed information on material properties. For the necessary mathematical technique, reference can be made to K. J. Cox, D. K. Hamilton and C. J. R. Sheppard, "Observation of Optical Signatures of Materials", Appl. Physics Letters, 41(7), October 1982. Examples have been presented in this patent of applications of the invention to studies of thin films and to measurements of surface topography. It will be clear to those skilled in the art that the same technique can be applied to the measurement of any property which results in a perturbation of the acoustic propagation conditions at the specimen surface. For example, the presence of residual stress affects the propagation velocity of the Rayleigh waves, and it has been demonstrated that sensitive measurements of surface stress can be made on a microscopic scale using this invention. Further examples include the measurement of impurity concentration in semiconductors, the presence of microcracks too small to be otherwise detected in ceramics, the distribution of constituent components in metal alloys, etc.

We claim:

1. In an acoustic microscope, means for measuring the surface characteristics of a sample by measuring in surface wave velocity in said sample, comprising transducer means for generating normal on-axis and off-axis rays toward a material surface; means for detecting the rays reflected from said surface in response to said normal and off-axis rays;

means for measuring the phase difference between on-axis and off-axis reflected rays to establish the surface characteristics of the material.

2. A system as claimed in claim 1 further including means for positioning said sample at the focal point of said acoustic transducer.

3. A system as claimed in claim 1 wherein positioning means positions said sample between said focal point and said transducer means, the focal point thereby being below the surface of said sample.

4. A system as claimed in claim 1 wherein said measuring means further comprising means for measuring the magnitude of the phase difference between the on-axis and off-axis reflected rays.

5. A system as claimed in claims 2 or 3 wherein said positioning means comprises feedback control means responsive to the ray-detection means for maintaining a constant distance between said transducer and said sample.

6. A system as claimed in claim 5 wherein said positioning means comprise means for establishing a temperature stable reference signal, means for detecting the phase of the on-axis signal, and phase responsive adjusting means for positioning either said transducer or said sample to maintain a constant phase relationship between said reference signal and said on-axis signal.

7. A system as claimed in claims 1 or 4 wherein said transducer means comprises a broad band transducer excited with a short duration pulse to facilitate time separation of the two ray paths.

8. A system as claimed in claims 1 or 4 wherein said measuring means comprises a synchronous phase detector for comparing the relative phase of said on-axis and off-axis rays received at said transducer from said sample.

9. A system as claimed in claim 8 wherein said phase detector includes a constant frequency generator, and including positioning means for positioning said sample relative to said transducer means for comparing the phase of the on-axis signal with the phase of the constant frequency generator signal, said positioning means adjusting the distance between said transducer and said sample to maintain the result of said phase comparison constant.

10. A system as claimed in claim 9 wherein said phase detector comprises means for combining the output of said constant frequency generator with said on-axis signal return and said off-axis signal return to establish first and second summation signals, the difference is phase of said first and second signals being established to define characteristics of the surface.

11. A system as claimed in claim 10 wherein said transducer means comprises first and second physically separate portions, said first portion transmitting said on-axis signal, said second portion transmitting said off-axis signal.

12. A system as claimed in claim 11 wherein said first portion comprises a relatively small center electrode and said second portion comprises a ring electrode substantially concentric with said small center electrode.

13. A system as claimed in claim 1 wherein
   said transducer comprises multiplex means for separately launching or detecting waves in different directions across said surface.

14. A system as claimed in claim 1 wherein said transducer has a broadband response characteristic, and said system comprises excitation means for exciting said transducer with a relatively short duration pulse, whereby said on-axis and off-axis signal responses are more easily separable.

15. In an acoustic microscope, a method of establishing the surface characteristics of a sample comprising
   (a) generating on-axis and off-axis signals toward the surface of a sample;
   (b) detecting and separating reflected return signals and, from said sample;
   (c) comparing the reflected return signals to establish the phase difference between the signals.

16. A method as claimed in claim 15 further including the steps of
   measuring the magnitude of the phase difference between reflected rays established by said on-axis and off-axis signals, and
   combining the magnitude and phase information to analyze the material characteristics of the surface under examination.

17. A method as claimed in claim 15 further including positioning said sample at the focal point of said acoustic transducer.

18. A method as claimed in claim 15 further including the step of positioning said sample between said focal point and said transducer means, the focal point thereby being below the surface of said sample.

19. A method as claimed in claim 18 wherein said positioning step comprises utilizing feedback control means responsive to the rays for maintaining a constant distance between said transducer and said sample.

20. A method as claimed in claim 19 wherein said feedback utilization step comprises establishing a temperature stable reference signal, detecting the phase of the reflection of the on-axis signal, and positioning either said transducer or said sample to maintain a constant phase relationship between said reference signal and said on-axis signal.

21. A method as claimed in claim 15 wherein said generating step comprises exciting a broad band transducer with a short duration pulse to facilitate time separation of the two ray paths.

22. A method as claimed in claim 19 wherein said generating step comprises exciting a broad band transducer with a short duration pulse to facilitate time separation of the two ray paths.

23. A method as claimed in claim 22 wherein said phase detector includes a constant frequency generator, and said positioning step includes comparing the phase of the on-axis signal with the phase of the constant frequency generator signal and adjusting the distance between said transducer and said sample to maintain the result of said phase comparison constant.

24. A method as claimed in claim 23 including the step of combining the output of said constant frequency generator with said on-axis signal return and said off-axis signal return to establish first and second summation signals, the difference in phase of said first and second signals being established to define characteristics of the surface.

* * * * *